US008906921B2

(12) United States Patent
MacDonald et al.

(10) Patent No.: US 8,906,921 B2
(45) Date of Patent: Dec. 9, 2014

(54) 4-ALKOXYPYRIDAZINE DERIVATIVES AS FAST DISSOCIATING DOPAMINE 2 RECEPTOR ANTAGONISTS

(75) Inventors: Gregor James MacDonald, Zoersel (BE); José Manuel Bartolomé-Nebreda, Toledo (ES)

(73) Assignee: Janssen Pharmaceutica NV, Beerse (BE)

( * ) Notice: Subject to any disclaimer, the term of this patent is extended or adjusted under 35 U.S.C. 154(b) by 8 days.

(21) Appl. No.: 12/597,166

(22) PCT Filed: Apr. 18, 2008

(86) PCT No.: PCT/EP2008/054731
§ 371 (c)(1),
(2), (4) Date: Oct. 22, 2009

(87) PCT Pub. No.: WO2008/128995
PCT Pub. Date: Oct. 30, 2008

(65) Prior Publication Data
US 2010/0063058 A1 Mar. 11, 2010

(30) Foreign Application Priority Data

Apr. 23, 2007 (EP) .................................. 07106704

(51) Int. Cl.
*A61K 31/50* (2006.01)
*C07D 237/02* (2006.01)
(52) U.S. Cl.
USPC .......................................... 514/247; 544/224
(58) Field of Classification Search
USPC .......................................... 544/224; 514/247
See application file for complete search history.

(56) References Cited

U.S. PATENT DOCUMENTS

| | | | |
|---|---|---|---|
| 3,933,823 A | 1/1976 | Denzel et al. |
| 3,933,832 A | 1/1976 | Langbein et al. |
| 4,126,689 A | 11/1978 | Sanczuk et al. |
| 4,197,304 A | 4/1980 | Sanczuk et al. |
| 4,585,471 A | 4/1986 | Forster et al. |
| 5,461,053 A | 10/1995 | Boigegrain et al. |
| 5,560,931 A | 10/1996 | Eickhoff et al. |
| 5,736,545 A | 4/1998 | Gadwood et al. |
| 5,866,589 A | 2/1999 | Romero et al. |
| 5,958,923 A | 9/1999 | Hellendahl et al. |
| 7,335,658 B2 | 2/2008 | Chakka et al. |
| 7,754,774 B2 | 7/2010 | Kobayashi et al. |
| 8,058,243 B2 | 11/2011 | Tyers et al. |
| 2007/0081953 A1 | 4/2007 | Dahms |
| 2008/0227791 A1 | 9/2008 | DeBruyn et al. |
| 2010/0063058 A1 | 3/2010 | MacDonald et al. |
| 2010/0069394 A1 | 3/2010 | MacDonald et al. |
| 2010/0076187 A1 | 3/2010 | MacDonald et al. |
| 2010/0092505 A1 | 4/2010 | Bianchi et al. |
| 2010/0120860 A1 | 5/2010 | MacDonald et al. |
| 2010/0137368 A1 | 6/2010 | MacDonald et al. |
| 2010/0210687 A1 | 8/2010 | Cooper et al. |
| 2011/0112107 A1 | 5/2011 | Bartolomé-Nebreda |
| 2011/0130408 A1 | 6/2011 | Bartolm-Nebreda et al. |

FOREIGN PATENT DOCUMENTS

| | | |
|---|---|---|
| CA | 2009501 | 8/1990 |
| DE | 2642856 | 3/1977 |
| DE | 3218482 | 11/1983 |
| EP | 0211457 | 2/1987 |
| EP | 281309 | 9/1988 |
| EP | 532178 | 3/1993 |
| EP | 1443046 | 8/2004 |
| EP | 1621538 | 2/2006 |
| EP | 1506185 | 5/2006 |
| GB | 1539473 | 1/1979 |
| WO | 95/18118 | 7/1995 |
| WO | 96/02249 | 2/1996 |
| WO | 96/18628 | 6/1996 |
| WO | 96/35666 | 11/1996 |
| WO | 97/43279 | 11/1997 |
| WO | 99/09025 | 2/1999 |
| WO | 99/36407 | 7/1999 |
| WO | 01/98273 | 12/2001 |
| WO | 02/068409 | 9/2002 |
| WO | 03/045353 | 6/2003 |
| WO | WO 03/049736 | 6/2003 |
| WO | 03/062215 | 7/2003 |
| WO | 03/066604 | 8/2003 |
| WO | 03/072548 | 9/2003 |
| WO | 2004/058729 | 7/2004 |
| WO | 2004/085406 | 10/2004 |
| WO | 2004/098555 | 11/2004 |
| WO | 2005/005779 | 1/2005 |
| WO | 2005/009976 | 2/2005 |
| WO | 2005/011655 | 2/2005 |
| WO | 2005/013907 | 2/2005 |
| WO | 2005/046581 | 5/2005 |
| WO | 2005/077914 | 8/2005 |
| WO | 2005/090317 | 9/2005 |
| WO | 2005/105779 | 11/2005 |
| WO | 2005/117883 | 12/2005 |

(Continued)

OTHER PUBLICATIONS

Vippagunta et al., "Crystalline solids", Adv. Drug Delivery Reviews 48 (2001) 3-26.*

(Continued)

*Primary Examiner* — Paul V. Ward
(74) *Attorney, Agent, or Firm* — Hal B. Woodrow

(57) ABSTRACT

The present invention relates to (1-benzyl-piperidin-4-yl)-(4-alkoxy-pyridazin-3-yl)-amines that are fast dissociating dopamine 2 receptor antagonists, processes for preparing these compounds, pharmaceutical compositions comprising these compounds as an active ingredient. The compounds find utility as medicines for treating or preventing central nervous system disorders, for example schizophrenia, by exerting an antipsychotic effect without motor side effects.

7 Claims, No Drawings

(56) References Cited

FOREIGN PATENT DOCUMENTS

| WO | 2005/123692 | 12/2005 |
|---|---|---|
| WO | 2005/123693 | 12/2005 |
| WO | WO 2006/034440 | 3/2006 |
| WO | 2006/055187 | 5/2006 |
| WO | WO 2007/001975 | 1/2007 |
| WO | WO 2007/048779 | 5/2007 |
| WO | 2007/130383 | 11/2007 |
| WO | 2008/068507 | 6/2008 |
| WO | 2008/098892 | 8/2008 |
| WO | WO 2010/012758 | 2/2010 |

OTHER PUBLICATIONS

Fryatt et al., J. Bioorganic and Medicinal Chemistry, 2004, 12, 1667-1687.
Goodman, A. J.; Standford, S. P.; Tarbit, B. Tetrahedron 1999, 55, 15067-15070.
Kikuchi et al., J. Med. Chem. (1999), 42 (4), 730-741.
Kapur et al., "Does fast dissociation from the dopamine D2 receptor explain the action of atypical antipsychotics?: A new hypothesis", Am. J. Psychiatry 2001, 158:3 p. 360-369.
Leysen et al., Journal of Receptor Research, 1984, 4(7), 817-845.
Moragues et al., "Dopaminergic Activity in a Series of N-Substituted 2-AMI Nopyrimidines" Farmaco, Edizione Scientifica, Societa Chimica Italiana, Pavia, IT, vol. 35, No. 11, 1980, pp. 951-964.
Schlachter et al. "Substituted 4-aminopiperidines having high in vitro affinity and selectivity for the cloned human dopami ne D4 receptor" European Journal of Pharmacology, vol. 322, 1997, pp. 283-286.
International Search Report for PCT/EP2008/054731 dated Sep. 30, 2008.
Written Opinion for PCT/EP2008/054731 dated Sep. 30, 2008.
Abbott, A., Nature, vol. 447, May 24, 2007, p. 368-370.
Bartoszyk et al., "Anxiolytic Effects of Dopamine Receptor Ligands: I. Involvement of Dopamine Autoreceptors" Life Sciences, Pergamon Press, Oxford, GB, vol. 62, No. 7, Jan. 1, 1998, pp. 649-663.
Contreras, Jean Marie, "Aminopyridazines as Acetylcholinesterase Inhibitors", J. Med. Chem. (1999),42 (4), 730-741.
Eichenberger, K.; Rometsch, R.; Druey, J. Australian Journal of Chemistry 1956, 9, 1755-1764 (see English abstract as provided).
Genin et al., "Synthesis and structure-activity relationships of the (alkylamino)piperidine-containing BHAP class of non-nucleoside reverse transcriptase inhibitors: effect of 3-alkylpyridine ring substitution" J. Med. Chem., vol. 42, No. 20, 1999, pp. 4140-4149.
Genin et al., "Synthesis and bioactivity of novel bis(heteroaryl)piperazine (BHAP) reverse transcriptase inhibitors: structure-activity relationships and increased metabolic stabilita of novel substituted pyri di ne' analogs" J. Med. Chem., vol. 39, No. 26, 1996, pp. 5267-5275.
Joyce et al., Drug Discovery Today, vol. 10, No. 13, Jul. 2005, pp. 917-925.
Kortagere et al., "Certain 1,4-disubstituted aromati c piperidines and piperazines with extreme selectivity for the Dopamine D4 receptor interact with a common receptor microdomain" Molecular Pharmacology, vol. 66, No. 6, 2004, pp. 1491-1499.
Kula et al., "Neuropharmacological assessment of potential dopamine D4 receptor-selective radioligands" European Journal of Pharmacology, Amsterdam, Nl, vol. 367, Jan. 1, 1999, pp. 139-142.
Mitchell et al., Pharmacology & Therapeutics 108 (2005), 320-333.
Munson et al., "Synthesis of 2-AlkYlamino-3-fluoropyridines Using Buchwald Conditions" Synthetic Communications, Taylor & Francis, Philadelphia, Pa. vol. 34, No. 5, Jan. 1, 2004, pp. 759-766.
Tao et al., Tetrahedron Letters 44 (2003) 7993-7996.
Yamada et al., Involvement of Septal and Striatal Dopamine D-2 Receptors in Yawning Behavior in Rats, Psychopharmacology, vol. 1, 1986, pp. 9-13.
Arlt, M. et al., Bioorganic & Medicinal Chemistry Letters; vol. 8; No. 15; p. 2033-2038, 1998.
Benjamin, et al., Biochemical Pharmacology; vol. 72; No. 6; p. 770-782, 2006.
Bianchi, "Current Issues in CNS drug" p. 1-3 (2011).
Binggeli et al., CA148:285064 (2008).
Braga et al., Roy. Soc. Chem. Chem. Commun. p. 3635-3645 (2005).
Cell Surface Receptor, Wikipedia, p. 1-6 (2012).
Chabner et al., Chemotherapy of Neoplastic Diseases, Neoplastic Agents in, Goodman & Gilman's: The Pharmacological Basis of Therapeutics 1315-1403, 1315 (L.L. Brunton et al., eds., 11th ed., 2006).
Cook et al., CA132_347492 (2000).
Dean et al., J. Org. Chem. 1993, 58, 7916-7917.
Garzya et al., Bioorganic & Medicinal Chemistry Letters, 17 (2007) 400-405.
Gillaspy et al., Tetrahedron Letters 1995, 36, 7399-7402.
Goodman and Gilman's The Pharmacologic Basis of Therapeutics, 12th Edition, Chapter 16, "Pharmacotherapy of Psychosis and Mania" by Jonathan M. Meyer, pp. 417-455, 2011.
Griesser, in Chapter 8, The Importance of Solvates (pp. 211-230), in the text, Polymorphism: In the Pharmaceutical Industry, Hilfiker, 2006.
Gundt et al., Bioorg. Med. Chem. Lett 17(3) 745-749 (2007).
Holenz et al., Drug discovery today; vol. 11; No. 7-8; p. 283-299, 2006.
Kapitulnik, J., Frontiers in Pharm. p. 1-2, (2011).
Kula et al., CA127:171455 (1997).
Kula et al., "RBI-257: A highly potent dopamine D receptor-selective ligand", European Journal of Pharmacology, 331 (1997), pp. 333-336.
Liu et al., Drug Development Research, 70: 145-168 (2009).
Lovenberg et al., Cloning of rat histamine H3 receptor reveals distinct species pharmacological profiles. J Pharmacol Expt Ther 2000;293:771-778.
Okuyama et al., Life Sci. 65(20) 2109-2125 (1999).
Phedias et al., CA148:509885 (2008).
Poupaert, J.H., Drug Design: Basic Principles and Applications, in 2 Encyclopedia of Pharmaceutical Technology 1362-1369, 1367 (James Swarbrick ed., 3rd ed., 2007).
Rodefer et al., Neuropsychopharmacology (2007), 1-10).
Seddon, K., Crystal. Growth & Design 4(6)1087 (2004).
TenBrink, CA124:8845 (1995).
Wood et al., Exp. Opin. Invest. Drugs 1696)771-775 (2007).
Xiao et al., Bioorg, Med. Chem. Lett. v.21, p. 861-864 (2011).
Zablotskaya et al., Chem. Het. Compo v.38 (7), p. 859-866 (2002).
Zhang et al., Exp. Opin. Ther. Patents 16(5) 587-630 (2006).
Fisas et al., British Journal of Pharmacology. 2006, 148: 973-983.
Hannon et al., Acta Biologica Szegediensis. 2002, 46(1-2): 1-12.

\* cited by examiner

4-ALKOXYPYRIDAZINE DERIVATIVES AS FAST DISSOCIATING DOPAMINE 2 RECEPTOR ANTAGONISTS

CROSS REFERENCE TO RELATED APPLICATIONS

This application claims priority from and is the national stage of PCT Application No. PCT/EP2008/054731, filed Apr. 18, 2008, which claims priority from European Patent Application No. 07106704.5, filed Apr. 23, 2007, the entire disclosures of which are hereby incorporated in their entirety.

FIELD OF THE INVENTION

The present invention relates to (1-benzyl-piperidin-4-yl)-(4-alkoxy-pyridazin-3-yl) -amines that are fast dissociating dopamine 2 receptor antagonists, processes for preparing these compounds, pharmaceutical compositions comprising these compounds as an active ingredient. The compounds find utility as medicines for treating or preventing central nervous system disorders, for example schizophrenia, by exerting an antipsychotic effect without motor side effects.

BACKGROUND PRIOR ART

J. Med. Chem. (1999), 42 (4), 730-741 discloses 6-phenyl-N-[1-(phenylmethyl)-4-piperidinyl]-3-pyridazinamine and analogous compounds as acetylcholinesterase inhibitors.

Farmaco, Vol. 35, no. 11, 1980, pages 951-964 discloses substituted N-[4-piperidinyl]-2-aminopyrimidines having dopaminergic activity, i.e. most of the disclosed compounds are agonists at the dopamine D2 receptor. Since none of the compounds tested antagonized the stereotyped behavior induced by a subsequent dose of apomorphine they may also be considered to be devoid of dopamine receptor blocking properties. The compounds of the present invention differ in the presence of a pyridazine instead of a pyrimidine moiety and the unexpected finding that they exert an antagonistic effect at the dopamine D2 receptor.

DESCRIPTION OF THE INVENTION

Schizophrenia is a severe and chronic mental illness that affects approximately 1% of the population. Clinical symptoms are apparent relatively early in life, generally emerging during adolescence or early adulthood. The symptoms of schizophrenia are usually divided into those described as positive, including hallucinations, delusions and disorganised thoughts and those referred to as negative, which include social withdrawal, diminished affect, poverty of speech and the inability to experience pleasure. In addition, schizophrenic patients are suffering from cognitive deficits, such as impaired attention and memory. The aetiology of the disease is still unknown, but aberrant neurotransmitter actions have been hypothesized to underlie the symptoms of schizophrenia. The dopaminergic hypothesis is one most often considered; it proposes that hyperactivity of dopamine transmission is responsible for the positive symptoms observed in schizophrenic patients. This hypothesis is based on the observation that dopamine enhancing drugs, such as amphetamine or cocaine, may induce psychosis, and on the correlation that exists between clinical doses of antipsychotics and their potency in blocking dopamine D2 receptors. All marketed antipsychotics mediate their therapeutic efficacy against positive symptoms by blocking the dopamine D2 receptor. Apart from the clinical efficacy, it appears that the major side effects of antipsychotics, such as extrapyramidal symptoms (EPS) and tardive dyskinesia, are also related to dopamine antagonism. Those debilitating side effects appear most frequently with the typical or first generation of antipsychotic (e.g., haloperidol). They are less pronounced with the atypical or second generation of antipsychotic (e.g., risperidone, olanzapine) and even virtually absent with clozapine, which is considered the prototypical atypical antipsychotic. Among the different theories proposed for explaining the lower incidence of EPS observed with atypical antipsychotics, the one that has caught a lot of attention during the last fifteen years, is the multireceptor hypothesis. It follows from receptor binding studies showing that many atypical antipsychotics interact with various other neurotransmitter receptors in addition to dopamine D2 receptors, in particular with the serotonin 5-HT2 receptors, whereas typical antipsychotic like haloperidol bind more selectively to the D2 receptors. This theory has been challenged in recent years because all major atypical antipsychotics fully occupy the serotonin 5-HT2 receptors at clinically relevant dosages but still differ in inducing motor side-effects. As an alternative to the multireceptor hypothesis, Kapur and Seeman ("Does fast dissociation from the dopamine D2 receptor explain the action of atypical antipsychotics?: A new hypothesis", Am. J. Psychiatry 2001, 158:3 p. 360-369) have proposed that atypical antipsychotics can be distinguished from typical antipsychotics by the rates at which they dissociate from dopamine D2 receptors. The fast dissociation from the D2 receptor would make an antipsychotic more accommodating of physiological dopamine transmission, permitting an antipsychotic effect without motor side effects. This hypothesis is particularly convincing when one considers clozapine and quetiapine. These two drugs have the fastest rate of dissociation from dopamine D2 receptors and they carry the lowest risk of inducing EPS in humans. Conversely, typical antipsychotics associated with a high prevalence of EPS, are the slowest dissociating dopamine D2 receptor antagonists. Therefore, identifying new drugs based on their rate of dissociation from the D2 receptor appears as a valid strategy to provide new atypical antipsychotics. An additional goal is to combine fast dissociating properties with selectivity for dopamine D2 receptors. The multiple receptor profile of current atypical antipsychotics is thought to be the cause of other side effects, such as weight gain and diabetes. Searching for selective D2 antagonists has been ignored as an approach for some time but it is our belief that using more selective compounds in clinic may reduce the occurrence of metabolic disorders associated with current atypical antipsychotic drugs.

It is the object of the present invention to provide novel compounds that are fast dissociating dopamine 2 receptor antagonists which have an advantageous pharmacological profile as explained hereinbefore, in particular reduced motor side effects, and moderate or negligible interactions with other receptors resulting in reduced risk of developing metabolic disorders.

This goal is achieved by the present novel compounds according to Formula (I):

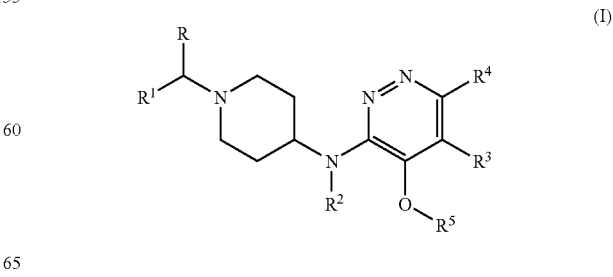

the pharmaceutically acceptable salts and solvates thereof, and stereoisomeric forms thereof, wherein R is hydrogen or $C_{1-6}$alkyl;

$R^1$ is phenyl; phenyl substituted with 1, 2 or 3 substituents each independently selected from the group consisting of halo, cyano, $C_{1-4}$alkyl, $C_{1-4}$alkyloxy, perfluoro $C_{1-4}$alkyl, and perfluoro$C_{1-4}$alkyloxy; thienyl; thienyl substituted with 1 or 2 substituents selected from the group consisting of halo and $C_{1-4}$alkyl;

$C_{1-4}$alkyl; $C_{1-4}$alkyl substituted with hydroxyl, $C_{3-8}$cycloalkyl or $C_{5-7}$cycloalkenyl;

$R^2$ is hydrogen or $C_{1-6}$alkyl;

$R^3$ is hydrogen, halo, $C_{1-4}$alkyl, trifluoromethyl or cyano;

$R^4$ is halo, trifluoromethyl or cyano; and $R^5$ is hydrogen, $C_{1-6}$alkyl, $C_{3-8}$cycloalkyl, $C_{3-8}$cycloalkyl$C_{1-4}$alkyl or perfluoro$C_{1-4}$alkyl.

The compounds according to the invention are fast dissociating $D_2$ receptor antagonists. This property renders the compounds according to the invention especially suitable for use as a medicine in the treatment or prevention of schizophrenia, schizophreniform disorder, schizoaffective disorder, delusional disorder, brief psychotic disorder, shared psychotic disorder, psychotic disorder due to a general medical condition, substance-induced psychotic disorder, psychotic disorder not otherwise specified; psychosis associated with dementia; major depressive disorder, dysthymic disorder, premenstrual dysphoric disorder, depressive disorder not otherwise specified, Bipolar I disorder, bipolar II disorder, cyclothymic disorder, bipolar disorder not otherwise specified, mood disorder due to a general medical condition, substance-induced mood disorder, mood disorder not otherwise specified; generalized anxiety disorder, obsessive-compulsive disorder, panic disorder, acute stress disorder, post-traumatic stress disorder; mental retardation; pervasive developmental disorders; attention deficit disorders, attention-deficit/hyperactivity disorder, disruptive behaviour disorders; personality disorder of the paranoid type, personality disorder of the schizoid type, personality disorder of the schizotypical type; tic disorders, Tourette's syndrome; substance dependence; substance abuse; substance withdrawal; trichotillomania.

A person skilled in the art can make a selection of compounds based on the experimental data provided in the Experimental Part hereinafter. Any selection of compounds is embraced within this invention.

A first group of compounds relates to compounds of Formula (I), wherein R and $R^3$ are hydrogen, $R^4$ is chloro and $R^5$ is $C_{1-6}$alkyl.

A second group of compounds relates to compounds of Formula (I), wherein R and $R^3$ are hydrogen, $R^4$ is trifluoromethyl and $R^5$ is $C_{1-6}$alkyl.

A third group of compounds of Formula (I) are those wherein $R^2$ is hydrogen or methyl.

Amongst the compounds of Formula (I) and the stereoisomeric forms thereof, the most interesting are, for example, (6-Chloro-4-methoxy-pyridazin-3-yl)-[1-(3-fluoro-5-trifluoromethyl-benzyl)-piperidin-4-yl]-amine (E1);

(6-Chloro-4-methoxy-pyridazin-3-yl)-[1-(3,4-difluoro-benzyl)-piperidin-4-yl]-amine (E2);

(6-Chloro-4-methoxy-pyridazin-3-yl)-[1-(3,4,5-Trifluorobenzyl)-piperidin-4-yl]-amine (E3);

(4-Methoxy-6-trifluoromethyl-pyridazin-3-yl)-[1-(3-trifluoromethyl-benzyl)-piperidin-4-yl]-amine (E4);

(4-Methoxy-6-trifluoromethyl-pyridazin-3-yl)-[1-(3,5-difluoromethyl-benzyl)-piperidin-4-yl]-amine (E5);

(4-Methoxy-6-trifluoromethyl-pyridazin-3-yl)-[1-(3,4-difluoromethyl-benzyl)-piperidin-4-yl]-amine (E6);

(4-Methoxy-6-trifluoromethyl-pyridazin-3-yl)-[1-(3,4,5-trifluoromethyl-benzyl)-piperidin-4-yl]-amine (E7).

Throughout this application, the term "$C_{1-4}$alkyl" when used alone and when used in combinations such as "$C_{1-4}$alkyloxy", "perfluoro$C_{1-4}$alkyl", "di$C_{1-4}$alkylamino", includes, for example, methyl, ethyl, propyl, butyl, 1-methylpropyl, 1,1-dimethylethyl, the term; "perfluoro$C_{1-4}$alkyl" includes for example trifluoromethyl, pentafluoroethyl, heptafluoropropyl and nonafluorobutyl; "$C_{3-8}$cycloalkyl" includes cyclopropyl, cyclobutyl, cyclopentyl, cyclohexyl, cycloheptyl and cyclooctyl; "$C_{5-7}$cycloalkenyl" includes cyclopentenyl, cyclohexenyl and cycloheptenyl. The term halo includes fluoro, chloro, bromo, and iodo.

The pharmaceutically acceptable salts are defined to comprise the therapeutically active non-toxic acid addition salts forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, mandelic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid, pamoic acid and mandelic acid. Conversely, said salts forms can be converted into the free forms by treatment with an appropriate base.

The term solvates refers to hydrates and alcoholates which the compounds of Formula (I) may form.

The term "stereochemically isomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of Formula (I) are embraced within the scope of this invention.

The compounds of Formula (I) as prepared in the processes described below may be synthesized in the form of racemic mixtures of enantiomers that can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

Pharmacology

In order to find antipsychotic compounds active against positive symptoms and having an improved safety profile (low EPS incidence and no metabolic disorders), we have screened for compounds selectively interacting with the dopamine D2 receptor and dissociating fast from this receptor. Compounds were first screened for their D2 affinity in a binding assay using [$^3$H]spiperone and human D2L receptor cell membranes. The compounds showing an $IC_{50}$ less than 10 μM were tested in an indirect assay adapted from a method published by Josee E. Leysen and Walter Gommeren, Journal of Receptor Research, 1984, 4(7), 817-845, to evaluate their rate of dissociation.

The compounds were further screened in a panel of more than 50 common G-protein coupled receptors (CEREP) and found to have a clean profile, that is to have low affinity for the tested receptors.

Some of the compounds have been further tested in vivo models such as the "Antagonism of apomorphine induced agitation test in rats" and found to be orally active and bioavailable.

In view of the aforementioned pharmacology of the compounds of Formula (I), it follows that they are suitable for use as a medicine, in particular for use as an antipsychotic. More especially the compounds are suitable for use as a medicine in the treatment or prevention of schizophrenia, schizophreniform disorder, schizoaffective disorder, delusional disorder, brief psychotic disorder, shared psychotic disorder, psychotic disorder due to a general medical condition, substance-induced psychotic disorder, psychotic disorder not otherwise specified; psychosis associated with dementia; major depressive disorder, dysthymic disorder, premenstrual dysphoric disorder, depressive disorder not otherwise specified, Bipolar I disorder, bipolar II disorder, cyclothymic disorder, bipolar disorder not otherwise specified, mood disorder due to a general medical condition, substance-induced mood disorder, mood disorder not otherwise specified; generalized anxiety disorder, obsessive-compulsive disorder, panic disorder, acute stress disorder, post-traumatic stress disorder; mental retardation; pervasive developmental disorders; attention deficit disorders, attention-deficit/hyperactivity disorder, disruptive behaviour disorders; personality disorder of the paranoid type, personality disorder of the schizoid type, personality disorder of the schizotypical type; tic disorders, Tourette's syndrome; substance dependence; substance abuse; substance withdrawal; trichotillomania.

To optimize treatment of patients suffering from a disorder as mentioned in the foregoing paragraph, the compounds of Formula (I) may be administered together with other psychotropic compounds. Thus, in the case of schizophrenia, negative and cognitive symptoms may be targeted.

The present invention also provides a method of treating warm-blooded animals suffering from such disorders, said method comprising the systemic administration of a therapeutic amount of a compound of Formula (I) effective in treating the above described disorders.

The present invention also relates to the use of compounds of Formula (I) as defined hereinabove for the manufacture of a medicament, in particular an antipsychotic medicament, more especially a medicine in the treatment or prevention of schizophrenia, schizophreniform disorder, schizoaffective disorder, delusional disorder, brief psychotic disorder, shared psychotic disorder, psychotic disorder due to a general medical condition, substance-induced psychotic disorder, psychotic disorder not otherwise specified; psychosis associated with dementia; major depressive disorder, dysthymic disorder, premenstrual dysphoric disorder, depressive disorder not otherwise specified, Bipolar I disorder, bipolar II disorder, cyclothymic disorder, bipolar disorder not otherwise specified, mood disorder due to a general medical condition, substance-induced mood disorder, mood disorder not otherwise specified; generalized anxiety disorder, obsessive-compulsive disorder, panic disorder, acute stress disorder, post-traumatic stress disorder; mental retardation; pervasive developmental disorders; attention deficit disorders, attention-deficit/hyperactivity disorder, disruptive behaviour disorders; personality disorder of the paranoid type, personality disorder of the schizoid type, personality disorder of the schizotypical type; tic disorders, Tourette's syndrome; substance dependence; substance abuse; substance withdrawal; trichotillomania.

Those of skill in the treatment of such diseases could determine the effective therapeutic daily amount from the test results presented hereinafter. An effective therapeutic daily amount would be from about 0.01 mg/kg to about 10 mg/kg body weight, more preferably from about 0.05 mg/kg to about 1 mg/kg body weight.

The invention also relates to a pharmaceutical composition comprising a pharmaceutically acceptable carrier and, as active ingredient, a therapeutically effective amount of a compound according to Formula (I).

For ease of administration, the subject compounds may be formulated into various pharmaceutical forms for administration purposes. The compounds according to the invention, in particular the compounds according to Formula (I), a pharmaceutically acceptable acid or base addition salt thereof, a stereochemically isomeric form thereof, an N-oxide form thereof and a prodrug thereof, or any subgroup or combination thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing compounds of Formula (I) may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I) in pharmaceutical compositions, it can be advantageous to employ $\alpha$-, $\beta$- or $\gamma$-cyclodextrins or their derivatives, in particular hydroxyalkyl substituted cyclodextrins, e.g. 2-hydroxypropyl-$\beta$-cyclodextrin. Also co-solvents such as alcohols may improve the solubility and/or the stability of the compounds according to the invention in pharmaceutical compositions.

Preparation

Compounds of Formula (I) wherein R, $R^1$, $R^2$, $R^3$, $R^4$ and $R^5$ are as defined before, may be prepared by reacting a compound of Formula (II)

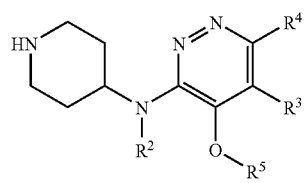

(II)

wherein $R^2$, $R^3$, $R^4$ and $R^5$ are as defined before, with a reagent of Formula $R^1$—CHW—R (III-a), where R and $R^1$ are as defined before and W represents a leaving group such as halo, e.g. chloro, bromo or iodo, or a sulfonyloxy group, e.g. methylsulfonyloxy, trifluoromethylsulfonyloxy, or methylphenylsulfonyloxy in the presence of a base such as diisopropylethylamine, in a suitable solvent such as acetonitrile and under suitable reaction conditions, such as a convenient temperature, either by conventional heating or under microwave irradiation for a period of time to ensure the completion of the reaction.

Alternatively, the compounds of Formula (I) wherein R, $R^1$, $R^2$, $R^3$, $R^4$ and $R^5$ are as defined before, could be prepared by reacting a compound of Formula (II) wherein $R^2$, $R^3$, $R^4$, and $R^5$ is as defined before, by reductive N-alkylation with a reagent of Formula $R^1$—C(=O)—R (III-b), where R and $R^1$ are as defined before, in the presence of a suitable reducing agent such as sodium triacetoxyborohydride, a suitable acid catalyst, such as acetic acid, in a suitable reaction inert solvent such as, 1,2-dichloroethane.

Compounds of Formula (II), wherein $R^2$, $R^3$, $R^4$ and $R^5$ are as defined before, may be prepared by deprotection of the protecting group in an intermediate of Formula (IV)

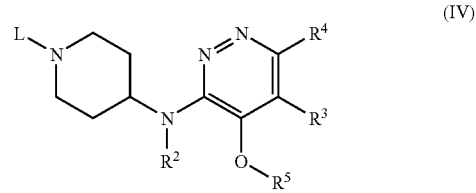

(IV)

where L represents a suitable protecting group, such as a tert-butoxycarbonyl, $R^2$, $R^3$, $R^4$ and $R^5$ are as defined before, under suitable conditions, such as reaction with Amberlyst® 15 ion exchange resin acidic form in methanol, when L represents a tert-butoxycarbonyl group.

Compounds of Formula (IV), wherein $R^2$, $R^3$, $R^4$ and $R^5$ are as defined before and L represents a suitable protecting group, may be prepared by reacting a compound of Formula (V)

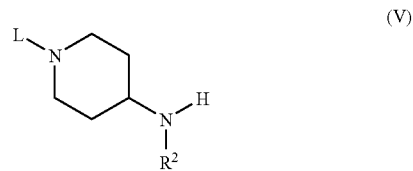

(V)

where $R^2$ is as defined before and L represents a suitable protecting group, such as tert-butoxycarbonyl, with a compound of Formula (VI)

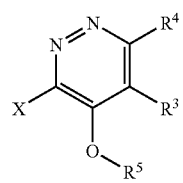

(VI)

where $R^3$, $R^4$ and $R^5$ are as defined before and X represents a halogen, in the presence of a base, such as cesium carbonate, a ligand, such as (R)-(+)-2,2'-bis (diphenylphosphino)-1,1'-binaphthyl, and a catalyst, such as palladium(II) acetate, in a suitable solvent, such as toluene, under suitable reaction conditions, such as a convenient temperature, either by conventional heating or under microwave irradiation for a period of time to ensure the completion of the reaction.

Compounds of Formula (VI) wherein $R^3$, $R^4$ and $R^5$ are as defined before and X represents a halogen, can be prepared by reacting a compound of Formula (VII)

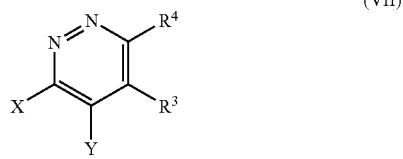
(VII)

where $R^3$ and $R^4$ are as defined before and X and Y represent a halogen with a reagent of Formula $R^5$—O-M (VIII), wherein $R^5$ is as defined before, and M represents a metal such as sodium, potassium or lithium in a suitable reaction inert solvent such as an alcohol of Formula $R^5$—OH (IX), for M=sodium or potassium, or tetrahydrofuran, for M=lithium, at temperatures typically ranging from −78° C. to room temperature. Specifically, a compound of Formula (VI) wherein $R^3$ is hydrogen, $R^4$ and X are chloro and $R^5$ is methyl, can be prepared by a procedure similar to that described in Eichenberger, K.; Rometsch, R.; Druey, J. Australian Journal of Chemistry 1956, 9, 1755-1764.

Compounds of Formula (VII) wherein $R^3$ is as defined before, $R^4$ and Y are chloro and X is a halogen may be prepared by reacting a compound of Formula (X)

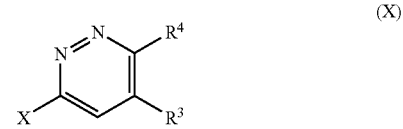
(X)

wherein $R^3$ is as defined before, $R^4$ is chloro and X represents a halogen, with sulfuryl chloride by a procedure similar to that described in Hanna, T. F.; Pettersson, I.; Gardipee, W. T.; Bray, K. C.; Green, S. J.; Slawin, A. M. Z.; Beall, H. D.; Moody, C. J. Bioorganic and Medicinal Chemistry 2004, 12, 1667-1687.

A compound of Formula (VII) wherein $R^3$ is as defined before, $R^4$ is as defined before but not chloro and X and Y represent a halogen can also be prepared by reacting a compound of Formula (XI)

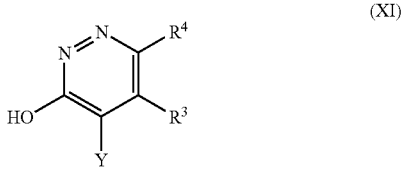
(XI)

wherein $R^3$ is as defined before, $R^4$ is as defined before but not chloro and Y represents a halogen, with a reagent of Formula P(=O)—$X_3$ (XII), where X is as defined before, under suitable reaction conditions, such as a convenient temperature, either by conventional heating or under microwave irradiation for a period of time to ensure the completion of the reaction.

A compound of Formula (XI) wherein $R^3$ is as defined before, $R^4$ is as defined before but not chloro and Y represents a halogen may be prepared by reacting a compound of Formula (XIII)

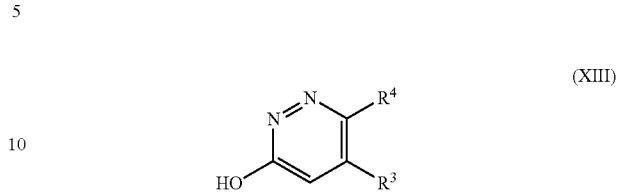
(XIII)

where $R^3$ is as defined before and $R^4$ is as defined before but not chloro, with a succinimide derivative of Formula (XIV),

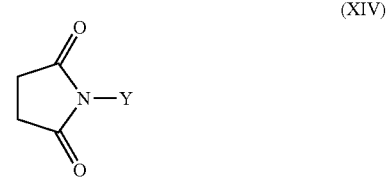
(XIV)

wherein Y represents an halogen, in the presence of an acid such as acetic acid, a suitable solvent, such as acetonitrile, under suitable reaction conditions, such as a convenient temperature, either by conventional heating or under microwave irradiation for a period of time to ensure the completion of the reaction.

A compound of Formula (XIII) where $R^3$ is as defined before and $R^4$ is as defined before but not chloro may be prepared by reacting a compound of Formula (XV)

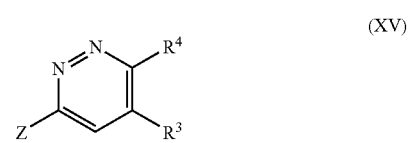
(XV)

wherein $R^3$ is as defined before and $R^4$ is as defined before but not chloro and Z represents an halogen, with a base such as sodium hydroxide, in a suitable reaction solvent such as water, under suitable reaction conditions, such as a convenient temperature, either by conventional heating or under microwave irradiation for a period of time to ensure the completion of the reaction.

A compound of Formula (XV) can be prepared by a procedure similar to that described in Goodman, A. J.; Standford, S. P.; Tarbit, B. Tetrahedron 1999, 55, 15067-15070 when $R^3$ is H, $R^4$ is trifluoromethyl and Z is chloro, by a procedure similar to that described in US05/034129 when $R^3$ is H, $R^4$ is cyano and Z is chloro or can be prepared by procedures known by any skilled person.

Compounds of Formula (I) wherein R, $R^1$, $R^2$, $R^3$, $R^4$ and $R^5$ are as defined before could also be prepared by reacting a compound of Formula (VI) wherein $R^3$, $R^4$ and $R^5$ are as defined before and X represents a halogen, with a piperidine derivative of Formula (XVI)

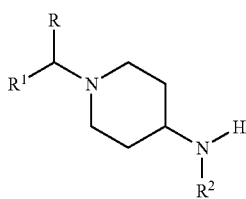

(XVI)

where R, R$^1$ and R$^2$ are as defined before, in the presence of a suitable base such as diisopropyethylamine, in a suitable solvent such as acetonitrile, and under suitable reaction conditions, such as a convenient temperature, either by conventional heating or under microwave irradiation for a period of time to ensure the completion of the reaction.

Compounds of Formula (XVI), where R, R$^1$ and R$^2$ are as defined before, may be prepared from a piperidin-4-ylcarbamic acid tent-butyl ester (XVII)

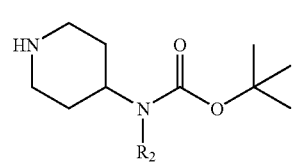

(XVII)

by reductive N-alkylation with a reagent of Formula R$^1$—C(═O)—R (III-b), where R and R$^1$ are as defined before, in the presence of a suitable reducing agent such as sodium triacetoxyborohydride, a suitable acid catalyst, such as acetic acid, in a suitable reaction inert solvent such as 1,2-dichloroethane, or in the presence of a suitable reducing agent, such as hydrogen, a suitable catalyst, such as palladium on carbon and in a suitable inert reaction solvent, such as methanol, followed by deprotection of the tert-butyloxycarbonyl group in an intermediate of Formula (XVIII), by treatment with an acid, such as trifluoroacetic acid, to give a compound of Formula (XVI) where R$^2$ is as defined before.

Alternatively, the compounds of Formula (XVI) wherein where R, R$^1$ and R$^2$ are as defined before could also be prepared by reacting a piperidin-4-ylcarbamic acid tert-butyl ester (XVII), with a reagent of Formula R$^1$—CHY—R (III-a), where R and R$^1$ are as defined before and Y represents a leaving group such as halo, e.g. chloro, bromo or iodo, or a sulfonyloxy group, e.g. methylsulfonyloxy, trifluoromethylsulfonyloxy, or methylphenylsulfonyloxy in the presence of a base such as diisopropylethylamine, in a suitable solvent such as such as dichloromethane, followed by deprotection of the tert-butyloxycarbonyl group in an intermediate of Formula (XVIII), by treatment with an acid, such as trifluoroacetic acid, to give a compound of Formula (XVI) where R$^2$ is as defined before.

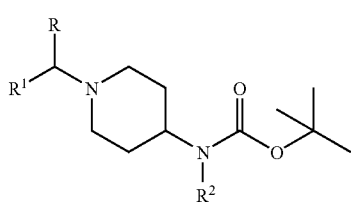

(XVIII)

Compounds of Formula (XVI), where R$^2$≠H, could be prepared by reacting a compound of Formula (XIX)

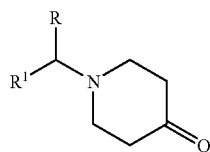

(XIX)

Where R and R$^1$ are as defined before, with an amine of Formula R$^2$—NH$_2$ (XX), in the presence of a suitable reducing agent, such as hydrogen, a suitable catalyst, such as palladium on carbon and in a suitable inert reaction solvent, such as ethanol.

Compounds of Formula (XIX), where R and R$^1$ are as defined before, may be prepared by reacting 4,4-ethylenedioxypiperidine (XXI)

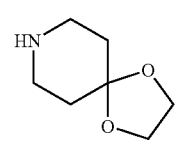

(XXI)

with a reagent of Formula R$^1$—C(═O)—R (III-b), where R and R$^1$ are as defined before, in the presence of a suitable reducing agent such as sodium triacetoxyborohydride, a suitable acid catalyst, such as acetic acid, in a suitable reaction inert solvent such as 1,2-dichloroethane, followed by deprotection of an intermediate of Formula (XXII)

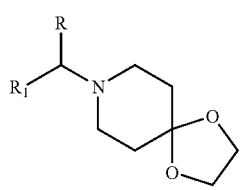

(XXII)

where R and R$^1$ are as defined before, by treatment with an acid, such as hydrochloric acid.

Experimental Part

Chemistry $^1$H spectra were recorded on a Bruker or a Bruker AV-500 spectrometers. The chemical shifts are expressed in ppm relative to tetramethylsilane.

Melting point determinations were performed on a Mettler FP62 apparatus.

The HPLC gradient was supplied by a HP 1100 from Agilent Technologies comprising a quaternary pump with degasser, an autosampler, a column oven (set at 40° C. except for Method 4 where temperature was set at 60° C.), a diode-array detector (DAD) and a column as specified in the respective methods below. Flow from the column was split to a MS detector. The MS detector was configured with an electrospray ionization source. Nitrogen was used as the nebulizer gas. The source temperature was maintained at 140° C. Data acquisition was performed with MassLynx-Openlynx software. Reversed phase HPLC was carried out on an XDB-C18 cartridge (1.8 μm, 2.1×30 mm) from Agilent, with a flow rate of 1 ml/min, at 60° C. The gradient conditions used are: 90% A (0.5 g/l ammonium acetate solution), 5% B (acetonitrile), 5% C (methanol) to 50% B and 50% C in 6.5 minutes, to 100% B at 7 minutes and equilibrated to initial conditions at 7.5 minutes until 9.0 minutes. Injection volume 2 μl. High-resolution mass spectra (Time of Flight, TOF) were acquired only in positive ionization mode by scanning from 100 to 750 in 0.5 seconds using a dwell time of 0.1 seconds. The capillary needle voltage was 2.5 kV and the cone voltage was 20 V. Leucine-Enkephaline was the standard substance used for the lock mass calibration.

Description 1
b 4-(6-Chloro-4-methoxy-pyridazin-3-ylamino)-piperidine-1-carboxylic acid tert-butyl ester (D1)

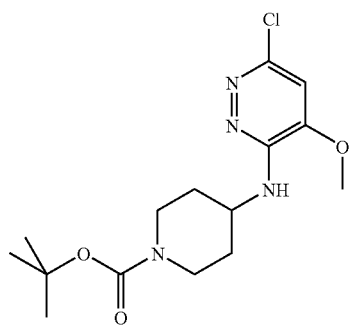

To a stirred solution of 3,6-dichloro-4-methoxy-pyridazine (0.73 g, 4.08 mmol) (prepared by a procedure similar to that described in Eichenberger, K.; Rometsch, R.; Druey, J. Australian Journal of Chemistry 1956, 9, 1755-1764), 4-amino-piperidine-1-carboxylic acid tert-butyl ester (0.98 g, 4.90 mmol) and cesium carbonate (2.66 g, 8.16 mmol) in toluene (15 ml) in a sealed tube under nitrogen, were added (R)-(+)-2,2'-bis (diphenylphosphino)-1,1'-binaphthyl (0.38 g, 0.61 mmol) and palladium(II) acetate (0.046 g, 0.20 mmol). The reactiom mixture was stirred at 110° C. for 18 h. After cooling to room temperature, the reaction mixture was filtered though Celite and the filtrate was evaporated. The crude product was purified by flash column chromatography (silica gel; 3% ammonia in methanol (7M)/dichloromethane). The desired fractions were collected and evaporated in vacuo. to yield D1 (0.44 g, 32%) as a yellow solid. $C_{15}H_{23}ClN_4O_3$ requires 342; Found 343 (MH$^+$).

Description 2
(6-Chloro-4-methoxy-pyridazin-3-yl)-piperidin-4-yl-amine (D2)

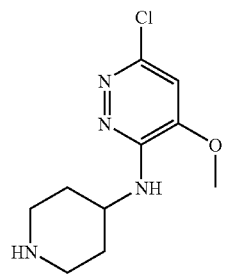 [SMILES: COc1cc(Cl)nnc1NC1CCNCC1]

A mixture of 4-(6-chloro-4-methoxy-pyridazin-3-ylamino)-piperidine-1-carboxylic acid tent-butyl ester (D1) (0.44 g, 1.27 mmol) and Amberlyst® 15 ion exchange resin, acidic form (4.1 mmol/g) (1.55 g, 6.35 mmol) in methanol (20 ml) was shaken at room temperature for 18 h. After this period, the mixture was filtered and then a 7M solution of ammonia in methanol was added. The mixture was shaken for 1 h, filtered and the filtrate evaporated in vacuo. The crude product was purified by flash column chromatography (silica gel; 3% ammonia in methanol (7M)/dichloromethane). The desired fractions were collected and evaporated in vacuo. to yield D2 (0.25 g, 81%) as a white solid. $C_{10}H_{15}ClN_4O$ requires 242; Found 243 (MH$^+$).

Description 3
6-Trifluoromethyl-pyridazin-3-ol (D3)

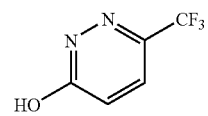

A mixture of 6-chloro-3-trifluoromethylpyridazine (10 g, 54.9 mmol) (prepared by following the procedure described in Goodman, A. J.; Stanforth, S. P.; Tarbit B. Tetrahedron 1999, 55, 15067-15070) and sodium hydroxide (8 g, 0.7 mmol) in water (150 ml) was stirred at reflux for 5 h. After this period, the solvent was evaporated in vacuo and the crude product dried at 60° C. under vacuum for 16 h. to yield D3, mixed with sodium chloride, (16.2 g,>100%) as a solid. $C_5H_3F_3N_2O$ requires 164; Found 165 (MH$^+$).

Description 4
4-Bromo-6-trifluoromethyl-pyridazin-3-ol (D4)

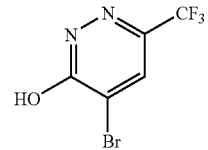 [SMILES: Oc1nnc(C(F)(F)F)cc1Br]

A mixture of 6-trifluoromethyl-pyridazin-3-ol (9.0 g, 54.9 mmol) (D3) and N-bromosuccinimide (12.7 g, 71.4 mmol) in a mixture of acetic acid (15 ml) and acetonitrile (350 ml) was stirred at 60° C. for 6 h. and at room temperature for a further 16 h. After this period, the reaction mixture was diluted with dichloromethane and extracted with a 10% solution of sodium thiosulfite. The organic layer was separated, dried (MgSO$_4$) and the solvent evaporated in vacuo to yield D4 (12.7 g, 95%) as a yellow solid. $C_5H_2BrF_3N_2O$ requires 243; Found 244 (MH$^+$).

Description 5
3,4-Dibromo-6-trifluoromethyl-pyridazine (D5)

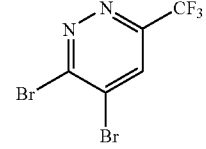 [SMILES: FC(F)(F)c1cc(Br)c(Br)nn1]

A mixture of 4-bromo-6-trifluoromethyl-pyridazin-3-ol (D3) (4.0 g, 16.4 mmol) and phosphorus oxybromide (28.2 g, 98.4 mmol) was stirred at 60° C. for 4 h. After this period, the reaction mixture was poured into a mixture of ice and water, diluted with dichloromethane and neutralized with a saturated solution of sodium hydrogen carbonate. The organic layer was separated, dried (MgSO₄) and the solvent evaporated in vacuo. The crude product was purified by flash column chromatography (silica gel; 3% ammonia in methanol (7M)/dichloromethane). The desired fractions were collected and evaporated in vacuo. to yield D5 (2.28 g, 46%) as a solid. $C_5HBr_2F_3N_2$ requires 305; Found 306 (MH⁺).

Description 6

3-Bromo-4-methoxy-6-trifluoromethyl-pyridazine (D6)

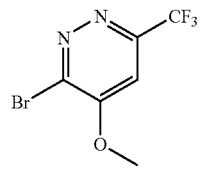

To a stirred solution of 3,4-dibromo-6-trifluoromethyl-pyridazine (D5) (1.48 g, 4.85 mmol) in methanol at 0° C., was added a 30% solution of sodium methoxide in methanol (0.8 ml, 4.67 mol). The reaction mixture was stirred at 0° C. for 1 h. After this period, the reaction mixture was neutralized by acetic acid addition and the solvent evaporated in vacuo. The crude product was purified by flash column chromatography (silica gel; 3% ammonia in methanol (7M)/dichloromethane). The desired fractions were collected and evaporated in vacuo. to yield D6 (0.79 g, 64%) as a solid. $C_6H_4BrF_3N_2O$ requires 257; Found 258 (MH⁺).

¹H NMR (400 MHz, CHLOROFORM-d) δ ppm 4.09 (s, 3H) 7.11 (s, 1H).

Description 7

4-(4-Methoxy-6-trifluoromethyl-pyridazin-3-ylamino)-piperidine-1-carboxylic acid tert-butyl ester (D7)

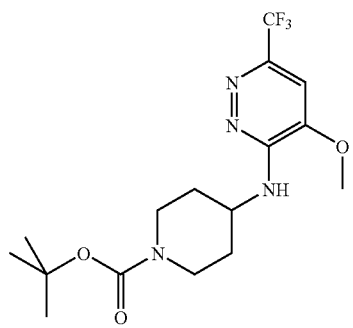 [SMILES: COc1cc(C(F)(F)F)nnc1NC1CCN(C(=O)OC(C)(C)C)CC1]

To a stirred solution of 3-bromo-4-methoxy-6-trifluoromethyl-pyridazine (D6) (0.79 g, 3.07 mmol), 4-amino-piperidine-1-carboxylic acid tert-butyl ester (0.74 g, 3.69 mmol) and cesium carbonate (2.0 g, 6.14 mmol) in toluene (15 ml) in a sealed tube under nitrogen, were added (R)-(+)-2,2'-bis(diphenylphosphino)-1,1'-binaphthyl (0.29 g, 0.46 mmol) and palladium(II) acetate (0.034 g, 0.15 mmol). The reactiom mixture was stirred at 110° C. for 18 h. After cooling to room temperature, the reaction mixture was filtered though Celite and the filtrate was evaporated. The crude product was purified by flash column chromatography (silica gel; 3% ammonia in methanol (7M)/dichloromethane). The desired fractions were collected and evaporated in vacuo. to yield D7 (0.73 g, 63%) as a yellow solid. $C_{16}H_{23}F_3N_4O_3$ requires 376; Found 377 (MH⁺).

Description 8

(4-Methoxy-6-trifluoromethyl-pyridazin-3-yl)-piperidin-4-yl-amine (D8)

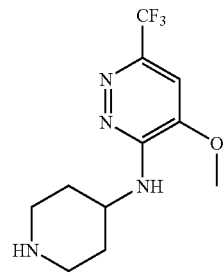

A mixture of 4-(4-Methoxy-6-trifluoromethyl-pyridazin-3-ylamino)-piperidine-1-carboxylic acid tent-butyl ester (D7) (0.73 g, 1.93 mmol) and Amberlyst® 15 ion exchange resin, acidic form (4.1 mmol/g) (2.35 g, 9.65 mmol) in methanol (20 ml) was shaken at room temperature for 18 h. After this period, the mixture was filtered and then a 7M solution of ammonia in methanol was added. The mixture was shaken for 1 h, filtered and the filtrate evaporated in vacuo. The crude product was purified by flash column chromatography (silica gel; 3% ammonia in methanol (7M)/dichloromethane). The desired fractions were collected and evaporated in vacuo. to yield D8 (0.49 g, 92%) as a yellow syrup. $C_{11}H_{15}F_3N_4O$ requires 276; Found 277 (MH⁺).

Example 1

(6-Chloro-4-methoxy-pyridazin-3-yl)₄₋₁-(3-fluoro-5-trifluoromethyl-benzyl)-piperidin-4-ylpamine (E1)

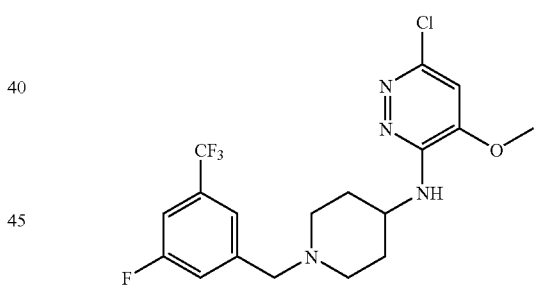

A mixture of (6-chloro-4-methoxy-pyridazin-3-yl)-piperidin-4-yl-amine (D2) (0.061 g, 0.25 mmol), 3-fluoro-5-trifluoromethyl-benzyl bromide (0.071 g, 0.27 mmol) and diisopropylethylamine (0.096 ml, 0.55 mmol) in acetonitrile (2 ml) was stirred at room temperature for 16 h. After this period, the solvent was evaporated in vacuo and the crude product purified by short open column chromatography (silica gel; 3% ammonia in methanol (7M)/dichloromethane). The desired fractions were collected and evaporated in vacuo and the crude product precipitated from diethyl ether to yield E1 (0.056 g, 54%) as a solid. $C_{18}H_{19}ClF_4N_4O$ requires 418; Found 419 (MH⁺). Rt: 4.66 min.

Melting point: 121.5° C.

¹H NMR (400 MHz, DMSO-d₆) δ ppm 1.54-1.67 (m, 2 H) 1.83-1.91 (m, 2 H) 2.06-2.15 (m, 2 H) 2.77-2.84 (m, 2 H) 3.59 (s, 2 H) 3.85-3.97 (m, 1 H) 3.91 (s, 3 H) 6.33 (d, J=7.88 Hz, 1 H) 7.00 (s, 1 H) 7.49 (d, J=9.74 Hz, 1 H) 7.53-7.59 (m, 2 H).

Example 4
(4-Methoxy-6-trifluoromethyl-pyridazin-3-yl)-[1-(3-trifluoromethyl-benzyl)-piperidin-4-yl]-amine (E4)

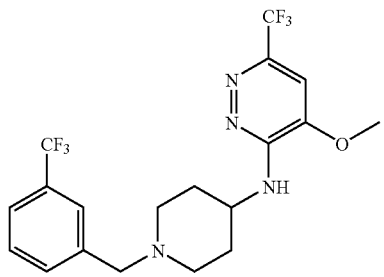 [SMILES: COc1cc(C(F)(F)F)nnc1NC1CCN(Cc2cccc(C(F)(F)F)c2)CC1]

A mixture of (4-methoxy-6-trifluoromethyl-pyridazin-3-yl)-piperidin-4-yl-amine (D8) (0.10 g, 0.36 mmol), 3-trifluoromethyl-benzyl bromide (0.060 ml, 0.29 mmol) and diisopropylethylamine (0.138 ml, 0.79 mmol) in acetonitrile (2 ml) was stirred at room temperature for 16 h. After this period, the solvent was evaporated in vacuo and the crude product purified by short open column chromatography (silica gel; 3% ammonia in methanol (7M)/dichloromethane). The desired fractions were collected and evaporated in vacuo. The product thus obtained was dissolved in a solution 2M of hydrochloric acid in diethyl ether to yield the corresponding hydrochloride salt E4 (0.138 g, 88%) as a solid. $C_{19}H_{20}F_6N_4O \cdot HCl$ free base requires 434; Found 435 (MH$^+$). Rt (Method 1): 4.73 min.

Melting point: 211.3° C.

$^1$H NMR (500 MHz, DMSO-$d_6$) δ ppm 1.95-2.25 (m, 4 H) 3.06-3.16 (m, 1.6 H) 3.19-3.25 (m, 0.6 H) 3.35-3.42 (m, 1.8 H) 3.99 (s, 2.4 H) 4.04 (s, 0.6 H) 4.21-4.30 (m, 1H) 4.41 (d, J=5.20 Hz, 1.6 H) 4.49 (d, J=5.78 Hz, 0.4 H) 6.98 (d, J=6.07 Hz, 0.2 H) 7.29 (s, 0.8 H) 7.33 (s, 0.2 H) 7.43-7.49 (m, 0.8 H) 7.72 (t, J=7.66 Hz, 1 H) 7.85 (d, J=7.80 Hz, 1 H) 7.95-8.00 (m, 1 H) 8.08 (s, 1 H) 10.96 (br. s., 1 H).

The following additional examples (E2-E3) were prepared from (D2) and the corresponding alkylating agents, by procedures similar to those described for Example (E1). The following additional examples (E5-E7) were prepared from (D8) and the corresponding alkylating agents, by procedures similar to those described for Example (E4). Examples (E4) and (E6) were isolated as the corresponding hydrochloric acid salts.

| Ex. | R$^1$ | R$^4$ | Melting Point (° C.) | Molecular Formula | M. Wt Free base | MH+ | RT (min) |
|---|---|---|---|---|---|---|---|
| E1 | 3,5-(F,CF$_3$)-phenyl | Cl | 121.5 | $C_{18}H_{19}ClF_4N_4O$ | 418 | 419 | 4.66 |
| E2 | 3,4-difluorophenyl | Cl | 130.5 | $C_{17}H_{19}ClF_2N_4O$ | 368 | 369 | 3.74 |
| E3 | 3,4,5-trifluorophenyl | Cl | 150.7 | $C_{17}H_{18}ClF_3N_4O$ | 386 | 387 | 4.24 |
| E4 | 3-CF$_3$-phenyl | CF$_3$ | 211.3 | $C_{19}H_{20}F_6N_4O \cdot HCl$ | 434 | 435 | 4.73 |

-continued

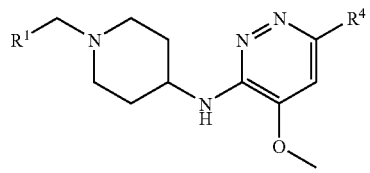

| Ex. | R¹ | R⁴ | Melting Point (° C.) | Molecular Formula | M. Wt Free base | MH+ | RT (min) |
|---|---|---|---|---|---|---|---|
| E5 | 3,5-difluorophenyl | CF₃ | 153.9 | $C_{18}H_{19}F_5N_4O$ | 402 | 403 | 4.52 |
| E6 | 3,4-difluorophenyl | CF₃ | 152.3 | $C_{18}H_{19}F_5N_4O \cdot HCl$ | 402 | 403 | 4.34 |
| E7 | 3,4,5-trifluorophenyl | CF₃ | 135.6 | $C_{18}H_{18}F_6N_4O$ | 420 | 421 | 4.71 |

Pharmacology

In vitro Binding Affinity for Human $D2_L$ Receptor

Frozen membranes of human Dopamine $D2_L$ receptor-transfected CHO cells were thawed, briefly homogenised using an Ultra-Turrax T25 homogeniser and diluted in Tris-HCl assay buffer containing NaCl, $CaCl_2$, $MgCl_2$, KCl (50, 120, 2, 1, and 5 mM respectively, adjusted to pH 7.7 with HCl) to an appropriate protein concentration optimised for specific and non-specific binding. Radioligand [³H]Spiperone (NEN, specific activity ~70 Ci/mmol) was diluted in assay buffer at a concentration of 2 nmol/L. Prepared radioligand (50 µl), along with 50 µl of either the 10% DMSO control, Butaclamol ($10^{-6}$ mol/l final concentration), or compound of interest, was then incubated (30 min, 37° C.) with 400 µl of the prepared membrane solution. Membrane-bound activity was filtered through a Packard Filtermate harvester onto GF/B Unifilterplates and washed with ice-cold Tris-HCl buffer (50 mM; pH 7.7; 6×0.5 ml). Filters were allowed to dry before adding scintillation fluid and counting in a Topcount scintillation counter. Percentage specific bound and competition binding curves were calculated using S-Plus software (Insightful). The compounds had a $pIC_{50}$ value>5.0.

Fast Dissociation

Compounds showing an $IC_{50}$ less than 10 µM were tested in an indirect assay adapted from a method published by Josee E. Leysen and Walter Gommeren, Journal of Receptor Research, 1984, 4(7), 817-845, to evaluate their rate of dissociation. Compounds at a concentration of 4 times their $IC_{50}$ were first incubated for one hour with human $D2_L$ receptor cell membranes in a volume of 2 ml at 25° C., then filtered over glass-fibre filter under suction using a 40 well multividor. Immediately after, the vacuum was released. 0.4 ml of pre-warmed buffer (25° C.) containing 1 nM [³H]spiperone was added on the filter for 5 minutes. The incubation was stopped by initiating the vacuum and immediate rinsing with 2×5 ml of ice-cold buffer. The filter-bound radioactivity was measured in a liquid scintillation spectrometer. The principle of the assay is based on the assumption that the faster a compound dissociates from the D2 receptor, the faster [³H] spiperone binds to the D2 receptor. For example, when D2 receptors are incubated with clozapine at the concentration of 1850 nM ($4×IC_{50}$), [³H]spiperone binding is equivalent to 60-70% of its total binding capacity (measured in absence of drug) after 5 min incubation on filter. When incubated with other antipsychotics, [³H]spiperone binding varies between 20 and 50%. Since clozapine was included in each filtration run, tested compounds were considered fast dissociating D2 antagonists if they were dissociating as fast or faster than clozapine. The compounds had a dissociation rate faster than that of clozapine, i.e. >50%.

The invention claimed is:
1. A compound of formula (I)

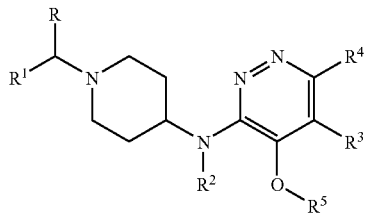

or a pharmaceutically acceptable salt or a solvate thereof, or a stereoisomeric form thereof, wherein R is hydrogen or $C_{1-6}$alkyl;

$R^1$ is phenyl; phenyl substituted with 1, 2 or 3 substituents each independently selected from the group consisting of halo, cyano, $C_{1-4}$alky, $C_{1-4}$alkyloxy, perfluoro $C_{1-4}$alkyl, and perfluoro$C_{1-4}$alkyloxy; thienyl; thienyl substituted with 1 or 2 substituents selected from the group consisting of halo or $C_{1-4}$alkyl;$C_{1-4}$alkyl; or $C_{1-4}$alkyl substituted with hydroxyl, $C_{3-8}$cycloalkyl or and $C_{5-7}$cycloalkenyl;

$R^2$ is hydrogen or $C_{1-6}$alkyl;

$R^3$ is hydrogen, halo, $C_{1-4}$alkyl, trifluoromethyl or cyano;

$R^4$ is halo, trifluoromethyl or cyano; and $R^5$ is hydrogen, $C_{1-6}$alkyl, $C_{3-8}$cycloalkyl; $C_{3-8}$cycloalkyl$C_{1-4}$alkyl or perfluoro$C_{1-4}$alkyl.

2. A compound according to claim 1, wherein R and $R^3$ are hydrogen, $R^4$ is chloro and $R^5$ is $C_{1-6}$alkyl.

3. A compound according to claim 1 wherein R and $R^3$ are hydrogen, $R^4$ is trifluoromethyl and $R^5$ is $C_{1-6}$alkyl.

4. A compound according to claim 1 wherein $R^2$ is hydrogen or methyl.

5. A compound according to claim 1 wherein the compound is selected from the group consisting of
(6-Chloro-4-methoxy-pyridazin-3-yl)-[1-(3-fluoro-5trifluoromethyl-benzyl)-piperidin-4-yl]-amine,
(6-Chloro-4-methoxy-pyridazin-3-yl)-[1-(3,4-difluorobenzyl)-piperidin-4-yl]-amine,
(6-Chloro-4-methoxy-pyridazin-3-yl)-[1-(3,4,5-Trifluoro-benzyl)-piperidin-4-yl]-amine,
(4-Methoxy-6-trifluoromethyl-pyridazin-3-yl)-[1-(3-trifluoromethyl-benzyl)-piperidin-4-yl]-amine,
(4-Methoxy-6-trifluoromethyl-pyridazin-3-yl)-[1-(3,5-difluoromethyl-benzyl)-piperidin-4-yl]-amine,
(4-Methoxy-6-trifluoromethyl-pyridazin-3-yl)-[1-(3,4-difluoromethyl-benzyl)-piperidin-4-yl]-amine and
(4-Methoxy-6-trifluoromethyl-pyridazin-3-yl)-[1-(3,4,5-trifluoromethyl-benzyl)-piperidin -4-yl]-amine.

6. A pharmaceutical composition comprising a therapeutically effective amount of a compound as defined in claim 1.

7. A pharmaceutical composition comprising a therapeutically effective amount of a compound as defined in claim 5.

* * * * *